United States Patent [19]

Praxl et al.

[11] 4,210,683

[45] Jul. 1, 1980

[54] PROCESS FOR PREPARING PESTICIDES RELEASING HYDROGEN PHOSPHIDE

[75] Inventors: Werner Praxl, Rimbach; Reiner Ehret, Weinheim, both of Fed. Rep. of Germany

[73] Assignee: Dr. Werner Freyberg Chemische Fabrik, Laudenbach, Fed. Rep. of Germany

[21] Appl. No.: 837,154

[22] Filed: Sep. 28, 1977

[30] Foreign Application Priority Data

Sep. 29, 1976 [DE] Fed. Rep. of Germany ....... 2643814

[51] Int. Cl.² .............................................. B05D 7/00
[52] U.S. Cl. .................................... 427/221; 424/40; 424/45; 424/78; 424/80; 424/128; 428/407
[58] Field of Search ................ 427/221, 220, 215; 428/403, 407; 424/128, 80, 78, 45, 40

[56] References Cited

U.S. PATENT DOCUMENTS

| 3,073,794 | 1/1963 | Stoner ................................. 424/80 |
| 3,132,067 | 5/1964 | Rauscher et al. .................. 424/128 |
| 3,238,096 | 3/1966 | Kaye ................................... 424/45 |
| 3,871,906 | 3/1975 | Sweeny et al. .................... 427/220 |
| 3,917,823 | 11/1975 | Kapp ................................. 424/128 |
| 3,969,547 | 7/1976 | Isawa et al. ....................... 427/221 |
| 4,013,790 | 3/1977 | Kapp ................................. 424/128 |

FOREIGN PATENT DOCUMENTS 51-1647  1/1976  Japan ...................................... 427/221

Primary Examiner—Shrive P. Beck
Assistant Examiner—Sadie L. Childs

[57] ABSTRACT

Process for preparing metal phosphide pesticide compositions which hydrolyze to release hydrogen phosphide in which the pesticide is coated with a water soluble polymer.

11 Claims, No Drawings

PROCESS FOR PREPARING PESTICIDES RELEASING HYDROGEN PHOSPHIDE

BACKGROUND OF THE INVENTION

The present invention relates to a process for preparing pesticides which release hydrogen phosphide gas.

It is known that under the influence of water, certain phosphides of alkaline earth metals and earth metals such as calcium, magnesium and aluminum phosphide, will release hydrogen phosphide, a gas suitable for combatting pests. The above phosphides may be added in various forms, e.g., in bags, as tablets or other molded bodies, to the goods to be treated. Under the influence of moisture, hydrolysis will occur and phosphine is formed in an amount and at a rate useful for killing various pests.

The reaction rate is normally controlled by increasing the hydrophobicity of the phosphide, e.g., with hard paraffin, metal stearates, waxes, paraffin oils and the like. The use of such compounds is, however, disadvantageous as residues of the pesticidal composition still containing minor amounts of unreacted phosphide will not be wetted and decomposed when treated with water. Instead, the residues will float on the water surface and cannot even be wetted by stirring. Thus it is extremely difficult to decompose the phosphide under controlled conditions. There results the danger that decomposition may take place under conditions where the release of toxic hydrogen phosphide could be dangerous or even fatal.

Attempts have been made to avoid this undesirable result by employing small quantities of polyethylene oxides (PEO); see West German Offenlegungsschrift No. 2,443,333. As disclosed therein, the known film-forming PEO compounds will influence the decomposition rate in the desired extent without impairing the wettability of the composition.

Preparation of the pesticides as disclosed in the above publication is effected by mixing the individual components including PEO with exclusion of moist air, and subsequently compressing the mixture in order to obtain molded bodies, such as tablets, pellets and the like. Such molding normally requires the use of compacting agents such as organic fatty acids.

Experiments have, however, shown that the desired delay in the release of hydrogen phosphide gas can only be accomplished to a very limited degree when using PEO so that the handling of the pesticides may still be dangerous unless careful precautions are taken.

Moreover, technical difficulties are encountered in preparing molded bodies from such mixtures. The mixtures often have unsatisfactory flowability leading to variations in the weight of molded bodies and other disadvantages.

Molded bodies containing only small amounts of PEO are of moderate strength and quality.

Another important disadvantage is that molded bodies prepared in the described way have a tendency to self-ignite on contact with water.

It is an object of the present invention to overcome the above disadvantages and to provide pesticides which, with regard to preparation and use, comply with all essential criteria.

THE INVENTION

A process has now been discovered for preparing substantially dust free, free flowing compositions which release hydrogen phosphide gas and may be easily formed into dosage units, even without compacting agents. The process is characterized in that a finely divided phosphide of an alkaline earth metal or earth metal or a mixture of such phosphides with at least one conventional additive is coated with a water-soluble film of natural and/or synthetic polymers by dissolving the polymer in an anhydrous solvent, preferably of high volatility. The resulting solution is mixed with said pesticide and the solvent evaporated to provide the desired dust free, free flowing composition which may, if desired, be compressed to obtain molded bodies.

The process of the invention provides, e.g., phosphide-containing granulated materials which may be used directly as formed. Additionally, they may be subdivided into dosage units and compressed to hard and wear-resistant molded bodies. Residues of such pesticides remaining after release of hydrogen phosphide gas are easily wetted and destroyed with water. Because of its dust free, free flowing characteristics, in certain modes of application, the granulated material of the invention may be used as pesticides without further treatment, e.g. formation into tablets.

Amongst the convention additives which may be used in this invention are substances preventing self-ignition such as urea, ammonium carbamate, ammonium carbonate and the like, in amounts of about 10% to 50% by weight. Fillers such as NaCl, talcum, silicon oxide and the like, in an amount of about 0.5% by weight may also be employed.

Especially suited water soluble polymeric materials are: polymers of N-vinylpyrrolidone, polyethylene oxides, atactic polyvinyl methyl ethers, polyacrylamides, cellulose ethers, agar-agar, alginates etc. A wide variety of other water soluble polymers may also be employed.

In order to prepare such granulated materials, the selected film-forming compound is dissolved in a suitable anhydrous solvent, preferably a highly volatile solvent, and then mixed with the phosphide optionally containing additives. In the most simple embodiment of the present invention, said mixing is effected in a mixer or blender. During mixing, the solvent evaporates and the polymeric materials form a coating film on individual particles or groups of particles. A major advantage of the process of the invention is to be seen in the fact that the evaporating solvent protects the phosphide from environmental humidity during the mixing operation. When employing solvents of lower volatility, a drying step or preparation under a vacuum may be advisable.

The following solutions of polymers were found to be especially suited:
- 5% to 10% by weight of polyvinylpyrrolidone having a molecular weight of 30,000 to 1,000,000 in dichloromethane;
- 5% to 10% by weight of vinylpyrrolidone-vinylacetate copolymer (VP/VA ratio=70/30 to 20/80) in ethylacetate;
- 2% by weight of methylhydroxypropyl cellulose in dichloromethanemethanol mixtures (ratio=70/30 to 90/10);
- 10% by weight of polyethylene oxide having a molecular weight of 4,000 to 20,000 in tetrachloromethane.

Solutions of cellulose ethers, polyacrylamides, polyvinylmethyl ethers and agar-agar are also useful. Examples of suitable solvents are: acetone, isobutanol, isobutylacetate, chloroform, Frigen 11 and Frigen 113 which are, respectively, trichlorofluoromethane and trichlorotrifluoroethane.

Although, as indicated above, the products of the invention can be used without the formation of tablets or pellets, such molded bodies can be prepared by conventional procedures without the use of compacting agents. Surprisingly, such products have excellent compression strength and form stability. Moreover, their rate of gas release can be controlled to the desired rate.

A special advantage of the products of this invention is that residues remaining after treatment of plants and the like are readily decomposed under safe conditions by treatment with water.

The following non-limiting examples are given by way of illustration only.

EXAMPLE I

In a mixing apparatus, 7 kgs of aluminum phosphide, technical grade, were mixed with 2.7 kgs of ammonium carbamate. During the mixing, 0.3 kgs of polyvinylpyrrolidone (mol.wt. 900,000) dissolved in 3 kgs of dichloromethane were added. Total mixing time was 30 minutes. After evaporation of the solvent, a finely granulated, dust free material with good flowability was obtained. It could be compressed to tablets without further additives.

EXAMPLE II

In a continuous flow mixer, 55 parts of magnesium phosphide, technical grade, were mixed with 40 parts of ammonium carbamate, while 50 parts of a 10% solution of polyethylene oxide (mol.wt.=6,000) in carbon tetrachloride were introduced simultaneously. The final product was a finely grained, free-flowing material.

EXAMPLE III 60 parts of aluminum phosphide, technical grade, 20 parts of ammonium carbamate and 18 parts of urea were mixed while adding simultaneously 40 parts of a 5% solution of carboxypropyl cellulose in a solvent mixture comprising 8 parts of dichloromethane and 2 parts of methanol. After evaporation of the solvent, a fine granulated material was obtained.

In the following Table, properties of tablets prepared according to Example I are compared to the properties of tablets obtained by prior art methods.

Safety tests were carried out by placing 10 tablets, each weighing 3 grams, into a 400 ml beaker at room temperature and pouring 15 ml of water at a temperature of 22° C. over each sample.

The rate of gas release was determined under the following conditions:

Five tablets, each weighing 3 grams, were placed in a container having a capacity of ½ cubic meters while maintaining a temperature of 20° C. at a relative humidity of 60%. At the intervals listed in the Table, the hydrogen phosphide concentration was measured utilizing Draeger tubes.

TABLE

| | Tablets Prepared According to | |
|---|---|---|
| | Example I | Prior Art Method* |
| Hardness:* | 15 | 3-4 |
| Decomposition after | | |
| 60 minutes: | No change | Visibly decomposed |
| Safety test: | No ignition on 3 trials | 3 ignitions on 3 trials |
| Gas release: | | |
| After 30 min. | 25 ppm PH$_3$ | 35 ppm PH$_3$ |
| 60 min. | 50 ppm PH$_3$ | 150 ppm PH$_3$ |
| 2 hours | 75 ppm PH$_3$ | 250 ppm PH$_3$ |
| 3 hours | 125 ppm PH$_3$ | 400 ppm PH$_3$ |
| 4 hours | 420 ppm PH$_3$ | 700 ppm PH$_3$ |
| 24 hours | 2,150 ppm PH$_3$ | 2,150 ppm PH$_3$ |

*(70% AlP, technical grade, 26% ammonium carbamate, 4% polyethylene oxide)
*Measured with Monsanto hardness apparatus.

EXAMPLE IV

In a fluid bed spray granulator, 20 parts of aluminum phosphide, 40 parts of urea and 35 parts of NaCl were sprayed with 20 parts of a 1% solution of an atactic polyvinylmethyl ether having a k-value of 45 to 50 in toluene. The wetted material was then dried in a fluid bed by a countercurrent of moisture-free hot air. The resulting product was a dust-free, finely granulated material which could be employed as pesticides without further processing.

EXAMPLE V

In a silo compartment having a capacity of 102 cubic meters, 70 tons of hard wheat infested by Sitophilus granarius were treated with the granulated composition prepared in accordance with Example III. With the aid of a dosing chute, 20 grams of the composition were continuously added to each ton of wheat flowing into the silo. The wheat temperature was 18° C. and its moisture content 13.6%. After a period of 14 days, the pests had been killed off completely.

What is claimed is:

1. A method for the preparation of a pesticide composition which comprises forming a mixture of particles of a pesticide which releases hydrogen phosphide on exposure to water and selected from the group consisting of alkaline earth metal phosphides, earth metal phosphides and mixtures thereof with a solution of a water soluble polymer in an anhydrous solvent containing sufficient polymer to coat the surface of said particles upon evaporation of the solvent, and thereafter evaporating the solvent.

2. A method as in claim 1 wherein the polymer is a natural polymer.

3. A method as in claim 1 wherein the polymer is a synthetic polymer.

4. A method as in claim 3 wherein the polymer is selected from the group consisting of polyvinylpyrrolidone, vinylpyrrolidone-vinylacetate copolymers, methylhydroxypropyl cellulose, and polyethylene oxide.

5. A method as in claim 1 wherein the solvent is selected from the group consisting of dichloromethane, ethylacetate, tetrachloromethane, acetone, isobutanol, isobutylacetate, chloroform, trichlorofluoromethane, trichlorotrifluoroethane and dichloromethane-methanol mixtures in a weight ratio of from 70/30 to 90/10.

6. A method as in claim 8 wherein the solution contains from 1% to 10% polymer based on the weight of the solvent.

7. A method as in claim 6 wherein the solution contains from 5% to 10% polymer.

8. A method as in claim 1 wherein a conventional additive substance is incorporated in the mixture.

9. A method as in claim 8 wherein the additive is a self ignition preventing substance.

10. A method as in claim 9 wherein the additive is from 10 to 50% by weight of a material selected from the group consisting of urea, ammonium carbamate and ammonium carbonate.

11. A method as in claim 1 wherein the additive is from 0.5 to 60% by weight of a filler selected from the group consisting of sodium chloride, talcum and silicon dioxide.

* * * * *